(12) United States Patent
Tobin et al.

(10) Patent No.: US 11,739,043 B2
(45) Date of Patent: Aug. 29, 2023

(54) ILLUDIN ANALOGS, USES THEREOF, AND METHODS FOR SYNTHESIZING THE SAME

(71) Applicant: Lantern Pharma Inc., Dallas, TX (US)

(72) Inventors: Gregory J. Tobin, Frederick, MD (US); Shawn T. Blumberg, San Antonio, TX (US); Andrey D. Malakhov, Helotes, TX (US)

(73) Assignee: Lantern Pharma Inc., Plano, TX (US)

( * ) Notice: Subject to any disclaimer, the term of this patent is extended or adjusted under 35 U.S.C. 154(b) by 0 days.

(21) Appl. No.: 17/192,838

(22) Filed: Mar. 4, 2021

(65) Prior Publication Data

US 2021/0198191 A1    Jul. 1, 2021

Related U.S. Application Data

(63) Continuation of application No. PCT/US2019/049555, filed on Sep. 4, 2019, which is a continuation of application No. 62/726,914, filed on Sep. 4, 2018.

(51) Int. Cl.
*C07C 275/64* (2006.01)
*C07C 49/573* (2006.01)

(52) U.S. Cl.
CPC .......... *C07C 49/573* (2013.01); *C07C 275/64* (2013.01); *C07B 2200/07* (2013.01); *C07C 2603/94* (2017.05)

(58) Field of Classification Search
None
See application file for complete search history.

(56) References Cited

U.S. PATENT DOCUMENTS

| | | |
|---|---|---|
| 5,723,632 A | 3/1998 | Mcmorris |
| 5,932,553 A | 8/1999 | Mcmorris et al. |
| 7,655,695 B2 | 2/2010 | Mcmorris et al. |
| 2008/0306147 A1* | 12/2008 | McMorris ............... A61P 35/00 514/480 |
| 2016/0015658 A1 | 1/2016 | Kelner |
| 2018/0100197 A1 | 4/2018 | Knudsen |
| 2021/0230662 A1* | 7/2021 | Kulkarni ................. C12Q 1/42 |

OTHER PUBLICATIONS

McMorris ("Synthesis and Biological Activity of Enantiomers of Antitumor Irofulven" J. Org. Chern. 2004, 69, p. 619-623) (Year: 2004).*
PubChem Compound Summary for CID 11695183 (National Center for Biotechnology Information (2021); retrieved Aug. 5, 2021 from https://pubchem.ncbi.nlm.nih.gov/compound/11695183, available since Oct. 26, 2006) (Year: 2006).*
International Search Report, dated Feb. 7, 2020, from corresponding International Application No. PCT/US2019/049555.
Written Opinion of the International Searching Authority, dated Feb. 7, 2020, from corresponding International Application No. PCT/US2019/049555.

* cited by examiner

*Primary Examiner* — Amy C Bonaparte
(74) *Attorney, Agent, or Firm* — Greenberg Traurig, LLP; Nigamnarayan Acharya

(57) ABSTRACT

This invention provides illudin derivatives, intermediates, preparation methods, pharmaceutical compositions and uses thereof. Specific examples include novel synthetic routes to prepare illudin derivatives and an illudin derivative having a positive optical rotation, which has therapeutic value.

5 Claims, 7 Drawing Sheets

Scheme 3. New route(s) to (±)-acylfulvene (3), (±)-Irofulven (4) and (±)-LP-184 (5)

FIG. 1 (PRIOR ART)

Scheme 2. New route to pivitol intermediate (13)

FIG. 2

Scheme 3. New route(s) to (±)-acylfulvene (3), (±)-Irofulven (4) and (±)-LP-184 (5)

FIG. 9

ILLUDIN ANALOGS, USES THEREOF, AND METHODS FOR SYNTHESIZING THE SAME

CROSS-REFERENCE TO RELATED APPLICATIONS

This application is a continuation application of International Application No. PCT/US19/49555, filed Sep. 4, 2019, which claims the benefit of U.S. Provisional Patent Application No. 62/726,914, filed Sep. 4, 2018, which is incorporated herein by reference in its entirety.

TECHNICAL FIELD

This relates to illudin derivatives or analogs, intermediates, preparation methods, pharmaceutical compositions and uses thereof.

BACKGROUND

Illudins are a family of sesquiterpenes with antitumor antibiotic properties and are traditionally produced by various mushrooms. In their isolated form, illudins show selective toxicity for myelocytic leukemia and other malignant cells. *Omphalotus* species like *O. olearius* and *O. illudens* (Jack o' Lantern mushrooms), and *O. nidiformis* (Australian ghost fungus) produce the natural forms of Illudins. Illudins are highly toxic and have little therapeutic value in their natural forms.

Figure 1:
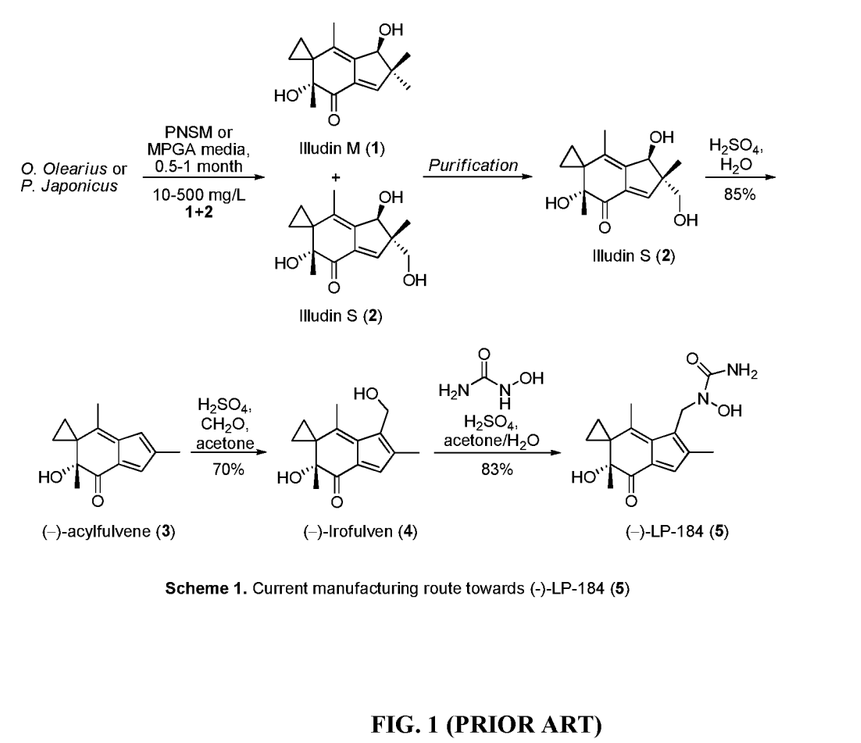
FIG. 1 shows a prior art current semi-synthetic pathway from Illudin S to hydroxymethylacylfulvene (HMAF) and (+) hydroxyureamethylacylfulvene.

Methods of manufacturing Illudin analogs have generally required the production of Illudin S from liquid growth of an *O. illudins* cell culture. FIG. 1 (prior art) shows the current semi-synthetic pathway from Illudin S to hydroxymethylacylfulvene (HMAF) and (+) hydroxyureamethylacylfulvene. Although *O. illudins* cell lines have been developed that produce a higher ratio of Illudin S to Illudin M, the production of this starting compound has been difficult in terms of expression yields, the time (e.g., >4 weeks of culture) required to begin harvesting Illudin S, contamination with Illudin M, and other complications including difficulties with reproducibility. The fermentation process can require the production, handling, and purification of large quantities of Illudin S which is highly toxic and represents a biohazard in the manufacturing facility.

Accordingly, there has been a pressing need for improved Illudins analogs and methods to synthesize the same.

SUMMARY

This invention provides illudin derivatives, intermediates, preparation methods, pharmaceutical compositions and uses thereof. Specific examples include novel synthetic routes to prepare illudin derivatives and an illudin derivative having a positive optical rotation, which has therapeutic value. The illudin derivatives react with DNA, which blocks the transcription process, which can effectively treat cancers and inflammatory diseases.

Another embodiment provides a synthetic pathway to acylfulvene, irofulven (6-hydroxymethylacylfulvene), UMAF and other analogs of compound I or illudin. A method of synthesizing compounds of formula (I) in which R1, R2 and R3 are independently (C1-C4) alkyl, methyl, or hydroxyl. In addition, the specific embodiments include derivations of enantiopure and racemic forms of acylfulvene, irofulven, and UMAF. The racemic and positive (+) entantiomer of UMAF are novel compounds as disclosed in the present invention.

DEFINITIONS

Unless defined otherwise, all technical and scientific terms used herein have the same meaning as is commonly understood by one of skill in art to which the subject matter herein belongs. As used herein, the following definitions are supplied in order to facilitate the understanding of the present invention.

As used herein, the terms a "patient," "subject," "individual," and "host" refer to either a human or a non-human animal suffering from or suspected of suffering from a disease or disorder associated with aberrant biological or cell growth activity.

The terms "treat" and "treating" such a disease or disorder refers to ameliorating at least one symptom of the disease or disorder. These terms, when used in connection with a condition such as a cancer, refer to one or more of: impeding growth of the cancer, causing the cancer to shrink by weight or volume, extending the expected survival time of the patient, inhibiting tumor growth, reducing tumor mass, reducing size or number of metastatic lesions, inhibiting the development of new metastatic lesions, prolonging survival, prolonging progression-free survival, prolonging time to progression, and/or enhancing quality of life.

The term "preventing" when used in relation to a condition or disease such as cancer, refers to a reduction in the frequency of, or delay in the onset of, symptoms of the condition or disease. Thus, prevention of cancer includes, for example, reducing the number of detectable cancerous growths in a population of patients receiving a prophylactic treatment relative to an untreated control population, and/or delaying the appearance of detectable cancerous growths in a treated population versus an untreated control population, e.g., by a statistically and/or clinically significant amount.

The term "pharmaceutically acceptable" means that, which is useful in preparing a pharmaceutical composition that is generally safe, non-toxic, and neither biologically nor otherwise undesirable and includes that which is acceptable for veterinary as well as human pharmaceutical use.

The term "stereoisomers" refers to any enantiomers, diastereomers, or geometrical isomers of the compounds of formula (I) wherever they are chiral or when they bear one or more double bond. When the compounds of the formula (I) and related formulae are chiral, they can exist in racemic or in optically active form. Since the pharmaceutical activity of the racemates or stereoisomers of the compounds according to the invention may differ, it may be desirable to use the enantiomers. In these cases, the end product or even the intermediates can be separated into enantiomeric compounds by chemical or physical measures known or employed as such in the synthesis.

The term "therapeutic effect" refers to a beneficial local or systemic effect in animals, particularly mammals, and more particularly humans, caused by administration of a compound or composition of the invention. The phrase "therapeutically-effective amount" means that amount of a compound or composition of the invention that is effective to treat a disease or condition caused by aberrant biological activity at a reasonable benefit/risk ratio.

The therapeutically effective amount of such substance will vary depending upon the subject and disease condition being treated, the weight and age of the subject, the severity of the disease condition, the manner of administration and the like, which can readily be determined by one of skill in the art.

DETAILED DESCRIPTION

An embodiment of the present application provides illudin derivatives, intermediates, preparation methods, pharmaceutical compositions and uses thereof. Specific examples include novel synthetic routes to prepare illudin derivatives and an illudin derivative having a positive optical rotation, which has therapeutic value. The illudin derivatives react with DNA, which blocks the transcription process, which can effectively treat cancers and inflammatory diseases.

One illustrative embodiment of this invention provides the compound with formula I:

(I)

The $R_1$, $R_2$ and $R_3$ are independently (C1-C4) alkyl, methyl, or hydroxyl Another illustrative embodiment includes hydroxymethylacylfulvene (HMAF, Irofulven), which has the following formula II

(II)

Yet another illustrative embodiment includes (−)-HydroxyUreaMethylAcylfulvene, (UMAF), which has the following formula III

(III)

One illustrative embodiment is characterized in that UMAF is the enantiomer, which exhibits at room temperature a positive optical rotation in dichloromethane or methanol. UMAF has a positive optical activity or may be part of a racemic mixture/mixture of UMAF structures. A mixture can include the following structures:

This application provides methods of synthesizing compounds of formula (IV):

(−) 6-hydroxymethylacylfulvene, HMAF, Irofulven

Another embodiment provides a synthetic pathway to acylfulvene, irofulven (6-hydroxymethylacylfulvene), UMAF and other analogs of compound I or illudin. A method of synthesizing compounds of formula (I) in which $R_1$, $R_2$ and $R_3$ are independently (C1-C4) alkyl, methyl, or hydroxyl. In addition, the specific embodiments include derivations of enantiopure and racemic forms of acylfulvene, irofulven, and UMAF. The racemic and positive (+) entantiomer of UMAF are novel compounds as disclosed in the present invention.

Figure 2:
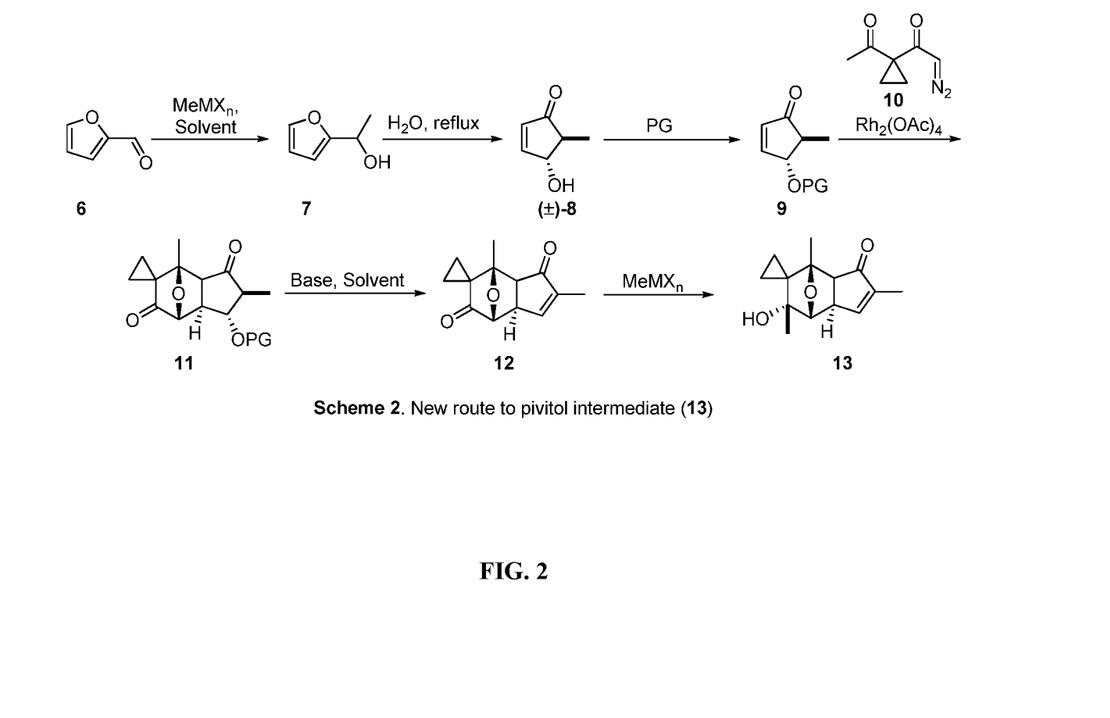
FIG. 2 shows one embodiment of this invention to prepare a pivitol intermediate or tertiary alcohol.

Referring now to FIG. 2, one embodiment includes the steps of (1) converting 2-furfural using a Grignard reaction, to produce an alcohol of the below formula in which $R_1$ is a hydrogen atom, methyl group, alkyl group, allyl or α-methylallyl group.

(2) Piancatelli rearrangement to the racemic cyclopentenone, and (3) protecting the alcohol group to furnish 9. In producing alcohols from carbonyl compounds by the Grignard reaction, a common practice is to prepare a Grignard reagent and then allow it to react with carbonyl compounds. The selection of appropriate protecting groups, can be readily determined by one skilled in the art—exemplary protecting groups include, but are not limited to, Silyl [trimethylsilane (TMS), tert-butyl, dimethylsilyl (TBS), acetates (Acetate (Ac), and benzoyl (Bz),] or benzyl [benzyl (Bn, para-methoxybenzyl (PMB)). Utilization of a carbonyl-ylide dipolar-cycloaddition between cyclopentenone 9 and diazoketone 10 provides the cycloadduct 11 which is transformed to 12 via base-mediated elimination. Selective alkylation of the ketone over the enone furnishes a pivitol intermediate: tertiary alcohol 13. removing the protecting group from the molecule (e.g., by base-mediated elimination). Selective alkylation of the ketone over the enone provides the tertiary alcohol.

Another embodiment provides a method for synthesizing acylfulvene (3), irofulven (4) and HydroxyUreaMethyl-Acylfulvene, (5) from a tertiary alcohol. The tertiary alcohol may be a racemate or an enantiopure form, would commence with the alkylation of 2-furfural (6) with methyl Grignard, followed by a Piancatelli rearrangement to the racemic cyclopentenone (±)-8 which would then be protected to furnish 9 (Scheme 2).

Figure 3:
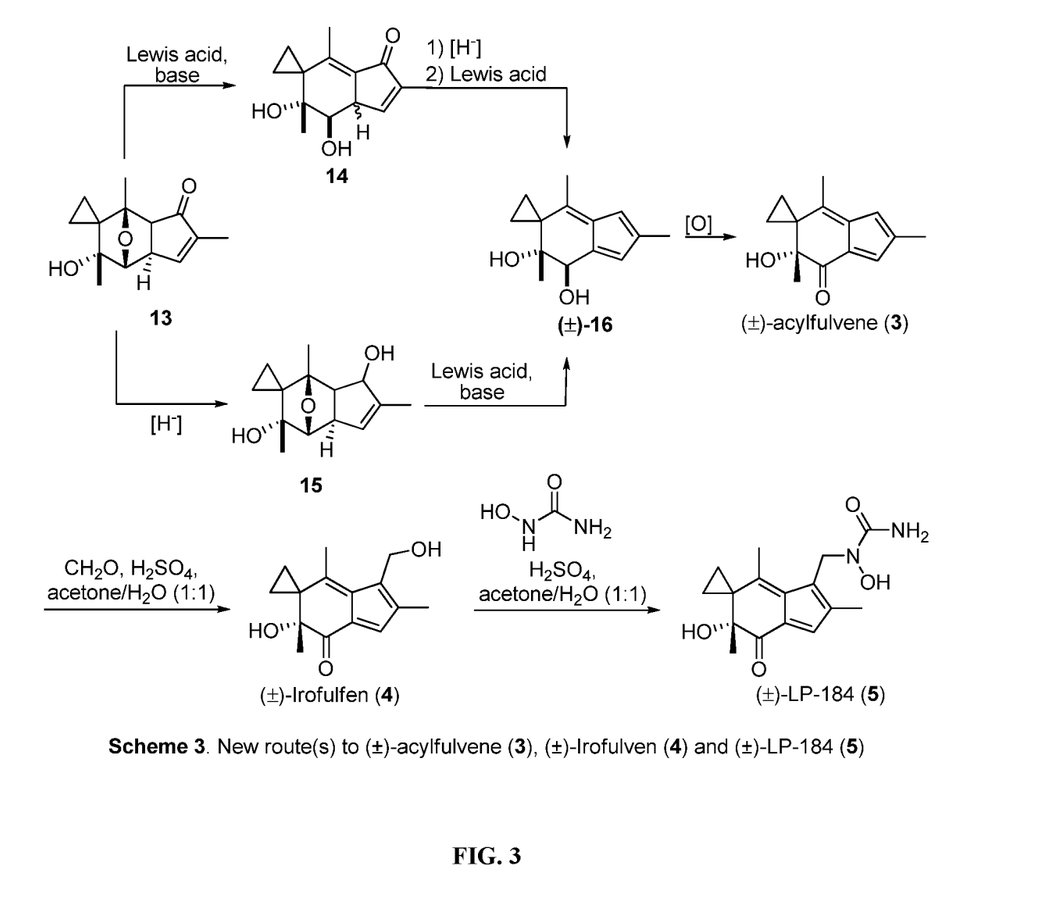
FIG. 3 shows another embodiment includes a method for synthesizing a compound into (±)-acylfulvene by two exemplary strategies.
Figure 4:
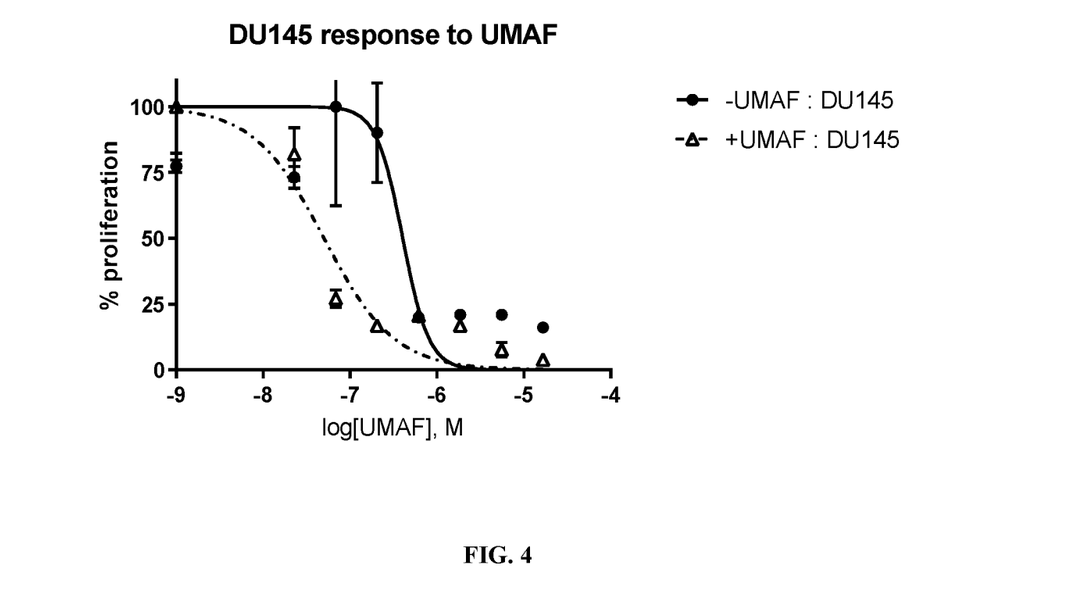
FIG. 4 show that the (+) enantiomer is more toxic to the DU145 cell line.

Referring now to FIG. 3, another embodiment includes a method for synthesizing compound 13 into (±)-acylfulvene (3) by two exemplary strategies (Scheme 3). In the one exemplary method, a Lewis acid-mediated elimination furnishes the dienone 14, which, after reduction and elimination of the ketone moiety, produces the diol (±)-16. The oxidation of compound (±)-16 then can result in (±)-acylfulvene (3). In another exemplary method, reduction of compound 13 yields alcohol 15, which after subjection to Lewis acidic conditions produces the diol (±)-16 and (±)-acylfulvene (3) is made in the same manner. In another example, (±)-irofulven (4) and (±)-UMAF (5) can then be made via a similar sequence described in Scheme 1. The disclosed transformation of 6 into acylfulvene (3), irofulven (4) and UMAF (5) may be the shortest and most efficient synthesis of these compounds to date.

If enantiopure acylfulvene (3), irofulven (4) or UMAF (5) are desired, a mixture or racemic intermediate (±)-16 can be purified via preparative chiral chromatography or other method known to those skilled in the art to produce both (+)-(16) and (−)-16 which can be used to synthesize either enantiomer of acylfulvene (3), Irofulven (4) or UMAF (5) (Scheme 4). This represents a process for the enantioselective synthesis of these compounds.

Scheme 4. New route to (+)-acylfulvene (3) and (−)-acylfulvene (3) using chiral resolution of (±)-16.

As shown below, either enantiomer of acylfulvene (3), Irofulven (4) or UMAF (5) can also be synthesized via the known enzymatic resolution of racemic (±)-9 to generate either (+)-9 or (−)-9, which can be converted to either acylfulvene (3), Irofulven (4) or UMAF (5) via the procedure described in Scheme 2 and 3 (Scheme 5).[1]

Specific embodiments also feature pharmaceutical compositions containing a pharmaceutically acceptable carrier and any compound of Formulas (I), (II), (III) and other compounds shown above.

Specific embodiments also feature compositions and compounds, e.g., UMAF, having reduced toxicity and side effects (including eye-related toxicities). Other embodiments allow for methods for treatment taking advantage of those properties.

Pharmaceutically acceptable salts of these compounds are also contemplated for the uses described herein. "Pharmaceutically acceptable salt" refers to any salt of a compound of the invention which retains its biological properties and which is not toxic or otherwise undesirable for pharmaceutical use. Pharmaceutically acceptable salts may be derived from a variety of organic and inorganic counter-ions well known in the art and include. Such salts include: (1) acid addition salts formed with organic or inorganic acids such as hydrochloric, hydrobromic, sulfuric, nitric, phosphoric, sulfamic, acetic, trifluoroacetic, trichloroacetic, propionic, hexanoic, cyclopentylpropionic, glycolic, glutaric, pyruvic, lactic, malonic, succinic, sorbic, ascorbic, malic, maleic, fumaric, tartaric, citric, benzoic, 3-(4-hydroxybenzoyl)benzoic, picric, cinnamic, mandelic, phthalic, lauric, methanesulfonic, ethanesulfonic, 1,2-ethane-disulfonic, 2-hydroxyethanesulfonic, benzenesulfonic, 4-chlorobenzenesulfonic, 2-naphthalenesulfonic, 4-toluenesulfonic, camphoric, camphorsulfonic, 4-methylbicyclo[2.2.2]-oct-2-ene-1-carboxylic, glucoheptonic, 3-phenylpropionic, trimethylacetic, tert-butylacetic, lauryl sulfuric, gluconic, benzoic, glutamic, hydroxynaphthoic, salicylic, stearic, cyclohexylsulfamic, quinic, muconic acid and the like acids; or (2) salts formed when an acidic proton present in the parent compound either (a) is replaced by a metal ion, e.g., an alkali metal ion, an alkaline earth ion or an aluminum ion, or alkali metal or alkaline earth metal hydroxides, such as sodium, potassium, calcium, magnesium, aluminum, lithium, zinc, and barium hydroxide, ammonia or (b) coordinates with an organic base, such as aliphatic, alicyclic, or aromatic organic amines, such as ammonia, methylamine, dimethylamine, diethylamine, picoline, ethanolamine, diethanolamine, triethanolamine, ethylenediamine, lysine, arginine, ornithine, choline, N,N'-dibenzylethylene-diamine, chloroprocaine, diethanolamine, procaine, N-benzylphenethylamine, N-methylglucamine piperazine, tris(hydroxymethyl)-aminomethane, tetramethylammonium hydroxide, and the like. Pharmaceutically acceptable salts further include, by way of example only, sodium, potassium, calcium, magnesium, ammonium, tetraalkylammonium and the like, and when the compound contains a basic functionality, salts of non-toxic organic or inorganic acids, such as hydrochloride, hydrobromide, tartrate, mesylate, besylate, acetate, maleate, oxalate and the like.

Pharmaceutical compositions of the invention comprise one or more compounds of the invention and one or more physiologically or pharmaceutically acceptable carrier. The term "pharmaceutically acceptable carrier" refers to a pharmaceutically-acceptable material, composition or vehicle, such as a liquid or solid filler, diluent, excipient, solvent or encapsulating material, involved in carrying or transporting any subject composition or component thereof. Each carrier must be "acceptable" in the sense of being compatible with the subject composition and its components and not injurious to the patient. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The compositions of the invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. In some embodiments, the compositions of the invention are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tween, Spans and other emulsifying agents or bioavailability enhancers which are commonly used in the manufacture of pharmaceutically acceptable solid, liquid, or other dosage forms may also be used for the purposes of formulation.

The pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

The pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of the compounds of the present invention that may be combined with the carrier materials to produce a composition in a single dosage form will vary depending upon the host treated, the particular mode of administration. The compositions should be formulated so that a dosage of between 0.01-100 mg/kg body weight/day of the inhibitor can be administered to a patient receiving these compositions.

In terms of dosage, toxicity and therapeutic efficacy of compounds of the invention, including pharmaceutically acceptable salts and deuterated variants, can be determined by standard pharmaceutical procedures in cell cultures or experimental animals. The $LD_{50}$ is the dose lethal to 50% of the population. The $ED_{50}$ is the dose therapeutically effective in 50% of the population. The dose ratio between toxic and therapeutic effects (LD50/ED50) is the therapeutic index. Compounds that exhibit large therapeutic indexes are preferred. While compounds that exhibit toxic side effects may be used, care should be taken to design a delivery system that targets such compounds to the site of affected tissue in order to minimize potential damage to uninfected cells and, thereby, reduce side effects. Alternatively, a second therapeutic agent can be administered to mitigate the toxic side effects of a primary treatment agent.

Data obtained from the cell culture assays and animal studies can be used in formulating a range of dosage for use in humans. The dosage of such compounds may lie within a range of circulating concentrations that include the $ED_{50}$ with little or no toxicity. The dosage may vary within this range depending upon the dosage form employed and the route of administration utilized. For any compound, the therapeutically effective dose can be estimated initially from cell culture assays. A dose may be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Examples

In the following examples, the following abbreviations are used therein.

| | |
|---|---|
| AcOH | Acetic acid |
| DIBAL-H | Diisobutylaluminium hydroxide |
| DIPEA | diisopropylethylamine |
| DMSO | Dimethylsulfoxide |
| IBX | 2-iodoxybenzoic acid |
| L | Liter |
| M | Molar |
| MeOAc | Methyl acetate |
| MeOH | Methanol |
| Mmol | milimole |
| MTBE | Methy tert-butyl ether |
| NMR | Nuclear Magnetic Resonance |
| TFA | Trifluoroacetic acid |
| THF | Tetrahyrofuran |
| TMS | tetramethylsilane |
| TMSOTf | trimethylsilyl trifluoromethanesulfonate |

Unless otherwise noted, solvents and reagents were used without purification. $CH_2Cl_2$ and MeCN were stored over 4 Å molecular sieves. Volatile solvents were removed under reduced pressure using a Buchi rotary evaporator. Thin layer chromatography (TLC) was performed on glass-backed pre-coated silica gel plates (0.25 mm thick with 60 F254) and were visualized using one or more of the following manners: UV light (254 nm), staining with 2 impregnated silica, $KMnO_4$ or Ceric Ammonium Molybdate (CAM). Flash chromatography was performed using the Biotage Isolera One using pre-loaded Silicycle 25 g high performance (14-40 μM) columns. $^1H$ nuclear magnetic resonance

(NMR) spectra were obtained at 400 MHz as indicated as solutions in CDCl3 with 0.05% v/v tetramethylsilane (TMS) unless indicated otherwise. $^{13}$C-NMR were obtained at 100 MHz as shown in the indicated deuterated solvent. Chemical shifts are reported in parts per million (ppm, δ), and referenced to TMS, and coupling constants are reported in Hertz (Hz). Spectral splitting patterns are designated as s, singlet; d, doublet; t, triplet; q, quartet; quint, quintuplet; sex, sextet; sept, septuplet; m, multiplet; comp, overlapping multiplets of magnetically nonequivalent protons; br, broad; and app, apparent.

1-acetylcyclopropanecarboxylic acid. tert-butyl 3-oxobutanoate (339 g, 350 mL, 2.146 mol) was added to a vigorously stirred mixture of $K_2CO_3$ (1186 g, 8.58 mol) and DMSO (3.5 L) in a flask. The mixture was stirred for 10 minutes whereupon neat 1,2-dibromoethane (806 g, 370 mL, 4.29 mol) was added and the mixture was stirred overnight. The reaction mixture was then diluted with $H_2O$ (2 L) and the mixture was extracted with MTBE (3×500 mL). The combined organic fractions were washed with 10% brine solution (4×200 mL) and the organic layer was dried over $Na_2SO_4$ and concentrated to an oil under reduced pressure. Neat TFA (486 g, 328 mL, 4.29 mol) was added to the oil and the mixture was stirred at room temperature overnight. The TFA was removed under reduced pressure and an aqueous solution of 20% (w/w) NaOH was added until the pH of the aqueous layer was <11. The mixture was then washed with MTBE (3×200 mL) and the aqueous layer was pH adjusted to >2 with an aqueous solution of 20% (w/w) H2SO4 and the mixture was extracted with $CH_2Cl_2$ (3×200 mL) and the combined organic layers were dried over $Na_2SO_4$ and concentrated under reduced pressure to recover 182 g (66%) of crude 1-acetylcyclopropanecarboxylic acid as an orange oil.

1-(furan-2-yl)ethan-1-ol. (7) A three neck round bottom flask (22 L) was washed with anhydrous THF (100 mL), evacuated and filled with nitrogen (3×). The flask was then charged with THF (1500 mL) and furfural (600.0 g, 547.2 mL, 6.244 mol) and the solution was cooled to 0° C. with an ice bath and kept under a nitrogen atmosphere. A solution of methylmagnesium chloride (2289 mL, 3 M, 6.838 mol) in THF was added slowly dropwise over ~180 min using a cannula using nitrogen pressure, carefully maintaining a reaction temperature less than 10° C. The mixture was allowed to cool to 0° C. and stirred for an additional 30 min before carefully quenching with 1N aq. HCl (1000 mL) with vigorous stirring, during which copious amounts of solids formed and the reaction mixture solidified. Water (2000 mL) was then added and the solids were agitated mechanically to break up the solids before adding an additional 1N aq. HCl (5000 mL) while carefully maintaining an internal temperature ≤10° C. The mixture was extracted with MTBE (3×1500 mL) and the organics were combined, washed with water (1000 mL), brine (1500 mL) then dried over sodium sulfate. The organic layer was then concentrated under reduced pressure by rotary evaporator to recover 678 g (96%) of crude 1-(furan-2-yl)ethan-1-ol as a ruby red liquid, which was taken on directly to the next step.

(±)-4-hydroxy-5-methylcyclopent-2-en-1-one. (8) A 2000 mL round bottom flask equipped with a reflux condenser and magnetic stir bar was charged with deionized water (1600 mL) and 1-(2-furyl)ethanol (7) (130 g, 1159 mmol). The reaction mixture was purged with nitrogen and the mixture was brought to reflux and was heated for 120 min with vigorous stirring. The reaction mixture was then allowed to cool to ambient temperature and the aqueous solution was decanted from the brown oily resin. The aqueous layer was then washed with a mixture of MTBE and hexanes (1:1, 3×250 mL) and the organic extracts were discarded. Sodium chloride (250 g) was then added to the aqueous solution and extracted with EtOAc (3×250 mL). The combined organic extracts were dried over sodium sulfate, filtered, and concentrated under reduced pressure on a rotary evaporator to recover 8.0 g (6%) of (±)-4-hydroxy-5-methylcyclopent-2-en-1-one (8) as a pale yellow oil.

(±)-4-(Methoxymethoxy)-5-methylcyclopent-2-en-1-one. (9) A flask was charged with (±)-4-hydroxy-5-methylcyclopent-2-en-1-one (8) (1.5 g, 13.38 mmol) $CH_2Cl_2$ (80 mL), and diisopropylethylamine (DIPEA) (5.19, 6.99 mL g, 40.14 mmol) and the mixture was purged with nitrogen and cooled to 0° C. with an ice bath. Chloromethyl methyl ether (3.14 M in MeOAc; 8.51 mL) was added dropwise via syringe over 20 min. The reaction was stirred for an additional hour at 0° C. before being allowed to slowly warm up to ambient temperature and stirring overnight. The reaction mixture was then diluted with $CH_2Cl_2$ (50 mL), quenched with 10% (aq) $NH_4Cl$ (50 mL) and the organics were separated. The aqueous layer was extracted with $CH_2Cl_2$ (50 mL) and the combined organic extracts were dried over sodium sulfate and concentrated under reduced pressure by rotary evaporator. The crude residue was purified by flash chromatography on silica gel (column: 40 g silicycle; Eluent: gradient $CH_2Cl_2$ 0→100% in hexane) to recover 10.5 g (84%) of (±)-4-(Methoxymethoxy)-5-methylcyclopent-2-en-1-one (9) as a pale yellow oil.

Diazoketone. (10) Oxalyl chloride (39.6 g, 26.4 mL, 312 mmol) was added to a solution of 1-acetylcyclopropanecarboxylic acid (20 g, 156 mmol) and DMF (110 mg, 0.12 mL, 1.5 mmol) in $CH_2Cl_2$ (200 mL) at room temperature and stirred for two hours. The reaction mixture was concentrated to an oil under reduced pressure and dissolved in anhydrous $CH_2Cl_2$ (300 mL) and cooled to −78° C. (dry ice/acetone bath). Neat 2,6-lutidine (19.3 g, 21.0 mL, 180 mmol) was added, followed by a solution of $TMSCHN_2$ (2.0 M, 200 mL, 300 mmol) in hexanes. The cooling bath was removed and the mixture was allowed to warm to room temperature and stir overnight. The mixture was concentrated to an oil under reduced pressure before adding MTBE (200 mL) and storing in the fridge for 30 min. The mixture was filtered through Celite (50 g), concentrated to an oil and purified on a silica plug (350 g, elute with 1000 mL $CH_2Cl_2$) and concentrating the eluent to recover 29.3 g of a deep red-brown oil which contained 11.23 g diazoketone (10) (49%) by NMR using mesitylene as an internal standard. The material was taken directly on to the next step.

Cycloadduct. (11) A stirring solution of diazoketone (10) (11.23 g, 73.8 mmol) and (±)-4-(Methoxymethoxy)-5-methylcyclopent-2-en-1-one (9) (5.76 g, 36.9 mmol) in $CH_2Cl_2$ was evacuated and filled with nitrogen (3×) before adding solid $Rh_2(OAc)_4$ (42 mg, 0.095 mmol) at room temperature and stirring overnight. The reaction was then concentrated under reduced pressure and purified by flash chromatography on silica gel (column: 120 g silicycle; Eluent: gradient EtOAc 0→80% in hexane) to recover 10.8 g (96%) by NMR using mesitylene as an internal standard. of Cycloadduct (11) as a waxy orange solid.

$^1$H-NMR (400 MHz) δ 4.96 (s, 1H), 4.80 (d, J=7.2 Hz, 1H), 4.74 (d, J=7.2 Hz, 1H), 3.96 (dd, J=8.0, 11.2 Hz, 1H), 3.45 (s, 3H), 2.93 (t, J=7.6 Hz, 1H), 2.67 (d, J=6.8 Hz, 1H), 2.59 (dq, J=6.4, 11.6 Hz, 1H), 1.30 (ddd, J=4.0, 6.8, 9.6 Hz, 1H), 1.20 (s, 3H). 1.16 (ddd, J=4.0, 6.4, 8.4 Hz, 1H). 1.12 (s, 3H), 1.07 (ddd, J=4.4, 7.6, 9.6 Hz, 1H), 0.73 (ddd, J=4.0, 7.2, 9.6 Hz, 1H); $^{13}$C-NMR (100 MHz) δ 212.8, 211.8, 96.2, 87.4, 81.5, 79.9, 59.5, 50.2, 44.1, 39.0, 14.2, 13.8, 12.4, 11.2.

NMR assignments: $^1$H-NMR (400 MHz) δ 4.96 (C9-H), 4.80 (C7-H), 4.74 (C7-H), 3.96 (C4-H), 3.45 (C8-H), 2.93 (C3-H), 2.67 (C2-H), 2.59 (C5-H), 1.30 (C14 or C15-H), 1.20 (C13-H). 1.16 (C14 or C15-H). 1.12 (C6-H), 1.07 (C14 or C15-H), 0.73 (C14 or C15-H); $^{13}$C-NMR (100 MHz) δ 212.8 (C1), 211.8 (C10), 96.2 (C7), 87.4 (C12), 81.5 (C9), 79.9 (C4), 59.5 (C2), 50.2 (C8, C5), 44.1 (C3), 39.0 (C11), 14.2 (C14 or C15), 13.8 (C13), 12.4 (C14 or C15), 11.2 (C6).

Methyladduct. Starting material (11) (5.6 g, 19.97 mmol) was dissolved in dry THF (80 mL) and cooled to −78° C. with a dry ice/acetone bath. The solution was put under vacuum and back-filled with nitrogen (2 times), whereupon a solution of MeMgCl (10 mL, 3 M in THF, 30 mmol; 1.5 eq) was added dropwise and the reaction was stirred at −78° C. for 3.5 h before quenching with acetic acid (1.3 mL). The reaction was warmed to room temperature, diluted with DCM (350 mL) and water (250 mL). The resulting mixture was separated. Aqueous phase was extracted with DCM (100 mL) and the combined organic extracts were washed with 20% aq. NaCl (100 mL) and dried over $Na_2SO_4$ and concentrated to an oil. The oil was purified via silica gel column chromatography (column: 40 g silicycle; Eluent: gradient EtOAc 0→45% in hexane) to recover 778 mg (13.2%) of methyladduct target product as a white crystalls, along with 2.23 g (39.8%) of starting material, 762 mg (12.9%) of second isomer and 833 g (13.5%) of bis methyl adduct for a total mass balance of 92.6%.

Cyclopentenone. (13) Potassium carbonate (704 mg, 5.09 mmol; 1.0 eq) was added to a solution of starting material (1.50 g, 5.09 mmol) in MeOH (60 mL) and the mixture was stirred at room temperature for 2 h before quenching with 10% aq. $NH_4Cl$ (10 mL) and diluted with EtOAc 300 mL. The resulting mixture was washed with 20% NaCl 100 mL. Organic layer was separated and washed with 20% NaCl (50 mL). The organic extract was dried over $Na_2SO_4$, concentrated to an oil and purified via silica gel column chromatography (column: 25 g silicycle; Eluent: gradient EtOAc 0→65% in hexane) to recover 974 mg (82%) of alkene Cyclopentenone (13) as a pale yellow crystals.

Dieneone. (14) Neat TMSOTf (7.72 mL, 9.48 g, 42.68 mmol) was added to a solution of bicycle (13) (2.0 g, 8.54 mmol) and 2,6-lutidine (7.46 mL, 6.86 g, 64.05 mmol) in dry CH$_2$Cl$_2$ (100 mL) at 0° C. and the solution was stirred for 4 hours under nitrogen atmosphere, whereupon the reaction was quenched with MeOH (4 mL) and the reaction mixture was concentrated to a red-orange oil under reduced pressure. The crude oil was suspended in MeOH (50 mL) and NH$_4$F (6.32 g, 170.8 mmol) and AcOH (8.55 mL, 8.97 g, 149.45 mmol) was added and the suspension was stirred at room temperature overnight. The reaction was then diluted with H$_2$O (250 mL), extracted with EtOAc (2×150 mL) and the organic layer was washed with 5% (aq) citric acid monosodium salt (2×100 mL), dried over Na$_2$SO$_4$, concentrated to an oil and purified via silica gel column chromatography (column: 25 g silicycle; Eluent: gradient EtOAc 0-55% in hexane) to recover 774 mg (39%) of the dieneone product (14) as a yellowish solid.

Diol. (16) A solution of dienone (14) (770 mg, 3.28 mmol) in dry CH$_2$Cl$_2$ (50 mL) was cooled to −78° C. with a dry ice/acetone bath before adding a solution of DIBAL-H (13.69 mL, 1.2 M in toluene, 16.43 mmol) in hexanes. The solution was stirred for 0.5 hours, whereupon the reaction was quenched with MeOH (4 mL) and the reaction mixture was concentrated to an oil under reduced pressure. In a separate flask, H$_2$O (1 mL) followed by H$_3$PO$_4$ (85% w/w in H$_2$O, 0.35 mL) was added to a vigorously stirred suspension of silica (10 g) in CH$_2$Cl$_2$ (50 mL) and the mixture was stirred at room temperature for 2 h. The solvent was then removed under reduced pressure until the silica was free-flowing. The crude oil from the DIBAL-H reduction was dissolved in EtOAc (200 mL) before adding H$_3$PO$_4$-doped hydrated silica (6.2 g) and the suspension was stirred vigorously for 3 h. The reaction was then quenched with TEA (430 μL, 312 mg, 3.08 mmol) and filtered. The resulting solution was concentrated to an oil and purified via silica gel column chromatography (column: 4 g silicycle; Eluent: gradient EtOAc 0-50% in hexane) to recover 83 mg (12%) of compound diol (16) as a yellow solid.

(−)-Acylfulvene. (3) Diol (16) (38 mg, 0.174 mmol) was dried azeotropically by dissolving in toluene (5 mL) and concentrating under reduced pressure before adding dry DMSO (6 mL) followed by IBX 45 wt. % (216 mg, 0.348 mmol) and the suspension was stirred at room temperature for 2 h. The mixture was then diluted with H$_2$O (15 mL), extracted with EtOAc (2×10 mL), dried over Na$_2$SO$_4$, concentrated to an oil and purified via silica gel column chromatography (column: 12 g silicycle; Eluent: gradient EtOAc 0-50% in hexane) to recover 37 mg (98%) of (−)-Acylfulvene (3) as a yellow gum.

$^1$H-NMR (400 MHz) δ 7.16 (d, J=0.8 Hz, 1H), 6.43 (quint, J=1.6 Hz, 1H), 3.93 (bs, 1H), 2.15 (d, J=1.2 Hz, 3H), 2.00 (s, 3H), 1.52 (ddd, J=4.0, 6.4, 9.6 Hz, 1H), 1.38 (s, 3H), 1.29 (ddd, J=4.8, 6.4, 9.6 Hz, 1H), 1.07 (ddd, J=5.2, 7.2, 9.6 Hz, 1H), 0.71 (ddd, J=4.0, 7.2, 9.6 Hz, 1H).

NMR assignments: $^1$H-NMR (400 MHz) δ 7.16 (C4-H), 6.43 (C1-H), 3.93 (O—H), 2.15 (C6-H), 2.00 (C11-H), 1.52 (C12 or C13-H), 1.38 (C14-H), 1.29 (C12 or C13-H), 1.07 (C12 or C13-H), 0.71 (C12 or C13-H).

(+)-Acylfulvene. (3) Diol (30 mg, 0.137 mmol) was dried azeotropically by dissolving in toluene (5 mL) and concentrating under reduced pressure before adding dry DMSO (5 mL) followed by IBX 45 wt. % (171 mg, 0.275 mmol) and the suspension was stirred at room temperature for 2 h. The mixture was then diluted with H$_2$O (15 mL), extracted with EtOAc (2×10 mL), dried over Na$_2$SO$_4$, concentrated to an oil and purified via silica gel column chromatography (column: 12 g silicycle; Eluent: gradient EtOAc 0-50% in hexane) to recover 30 mg (100%) of (+)-Acylfulvene as a yellow gum.

$^1$H-NMR (400 MHz) δ 7.16 (d, J=0.8 Hz, 1H), 6.43 (quint, J=1.6 Hz, 1H), 3.93 (bs, 1H), 2.15 (d, J=1.2 Hz, 3H), 2.00 (s, 3H), 1.52 (ddd, J=4.0, 6.4, 9.6 Hz, 1H), 1.38 (s, 3H), 1.29 (ddd, J=4.8, 6.4, 9.6 Hz, 1H), 1.07 (ddd, J=5.2, 7.2, 9.6 Hz, 1H), 0.71 (ddd, J=4.0, 7.2, 9.6 Hz, 1H).

(−)-Irofulven. (4) A suspension of paraformaldehyde (231 mg, 7.7 mmol as monomer) in 2M (aq) H$_2$SO$_4$ (4 mL) was heated to 90° C. for 30 min and cooled to room temperature before adding acetone (4 mL) and a solution of (−)-Acylfulvene (3) (37 mg, 0.171 mmol) in acetone (1 mL) and the mixture was stirred for 48 h at room temperature. The reaction was then diluted with H$_2$O (25 mL), extracted with CH$_2$Cl$_2$ (3×15 mL), and the combined organic extracts were washed with NaHCO$_3$ (aq) (15 mL) then H$_2$O (15 mL), water wash pH ~7. The organic extracts were then dried over Na$_2$SO$_4$, concentrated to an oil and purified via silica gel column chromatography (column: 12 g silicycle; Eluent: gradient EtOAc 0-65% in hexane) to recover 24.6 mg (58%) of (−)-Irofulven (4) as a yellow gum and 8.6 mg (23%) of recovered (−)-Acylfulvene.

¹H-NMR (400 MHz) δ 7.09 (s, 1H), 4.67 (d, J=12.4 Hz, 1H), 4.63 (d, J=12.4 Hz, 1H), 3.90 (bs, 1H), 2.19 (s, 3H), 2.15 (s, 3H), 1.49 (ddd, J=4.0, 6.0, 9.6 Hz, 1H), 1.38 (s, 3H), 1.36 (ddd, J=5.2, 6.4, 9.6 Hz, 1H), 1.08 (ddd, J=4.8, 7.2, 9.6 Hz, 1H), 0.72 (ddd, J=4.0, 7.6, 10.0 Hz, 1H).

NMR assignments: ¹H-NMR (400 MHz) δ 7.09 (C4-H), 4.67 (C15-H), 4.63 (C15-H), 3.90 (O—H), 2.19 (C6-H), 2.15 (C11-H), 1.49 (C12 or C13-H), 1.38 (C14-H), 1.36 (C12 or C13-H), 1.08 (C12 or C13-H), 0.72 (C12 or C13-H).

(+)-Irofulven. (4) A suspension of paraformaldehyde (186 mg, 6.21 mmol as monomer) in 1M (aq) H$_2$SO$_4$ (9 mL) was heated to 90 QC for 30 min and cooled to room temperature before adding acetone (9 mL) and a solution on (+)-Acylfulvene (3) (30 mg, 0.138 mmol) in acetone (3 mL) and the mixture was stirred for 72 h at room temperature. The reaction was then diluted with H$_2$O (30 mL), extracted with CH$_2$Cl$_2$ (3×15 mL) and the combined organic extracts were washed with NaHCO$_3$ (aq) (15 mL) then H$_2$O (15 mL), water wash pH ~7. The organic extracts were then dried over Na$_2$SO$_4$, concentrated to an oil and purified via silica gel column chromatography (column: 12 g silicycle; Eluent: gradient EtOAc 0-65% in hexane) to recover 12.7 mg (37%) of (+)-Irofulven as a yellow gum and 12.4 mg (41%) of recovered (+)-Acylfulvene (3).

¹H-NMR (400 MHz) δ 7.09 (s, 1H), 4.67 (d, J=12.4 Hz, 1H), 4.63 (d, J=12.4 Hz, 1H), 3.90 (bs, 1H), 2.19 (s, 3H), 2.15 (s, 3H), 1.49 (ddd, J=4.0, 6.0, 9.6 Hz, 1H), 1.38 (s, 3H), 1.36 (ddd, J=5.2, 6.4, 9.6 Hz, 1H), 1.08 (ddd, J=4.8, 7.2, 9.6 Hz, 1H), 0.72 (ddd, J=4.0, 7.6, 10.0 Hz, 1H).

NMR assignments: ¹H-NMR (400 MHz) δ 7.09 (C4-H), 4.67 (C15-H), 4.63 (C15-H), 3.90 (O—H), 2.19 (C6-H), 2.15 (C11-H), 1.49 (C12 or C13-H), 1.38 (C14-H), 1.36 (C12 or C13-H), 1.08 (C12 or C13-H), 0.72 (C12 or C13-H).

(−)-hydroxyureamethylacylfulvene. (5) Hydroxyurea (37 mg, 0.487 mmol) was added to a solution of (−)-Irofulven (4) (24 mg, 0.097 mmol) in a mixture of acetone (1.5 mL) and 2M (aq) H$_2$SO$_4$ (1.5 mL) and the mixture was stirred for 24 h at room temperature before diluting with H$_2$O (15 mL) and EtOAc (15 mL), organics were separated and aqueous layer was extracted with EtOAc (2×10 mL). The combined organic extracts were washed with 5% NaHCO$_3$ (aq) (10 mL) the brine (10 mL). The organic extracts were then dried over Na$_2$SO$_4$, concentrated to an oil and purified via silica gel column chromatography (column: 12 g silicycle; Eluent: gradient EtOAc 10-95% in hexane) to recover 18.9 mg (61%) of (−)-LP-184 (5) as a yellow-orange solid.

¹H-NMR (400 MHz) δ 7.03 (s, 1H), 6.86 (s, 1H), 5.37 (bs, 2H), 4.80 (d, J=14.8 Hz, 1H), 4.52 (d, J=14.5 Hz, 1H), 3.84 (bs, 1H), 2.17 (s, 3H), 2.08 (s, 3H), 1.47 (ddd, J=4.0, 6.4, 10.0 Hz, 1H), 1.35 (ddd, J=5.2, 6.4, 9.6 Hz, 1H), 1.35 (s, 3H), 1.34 (ddd, J=5.2, 7.6, 9.6 Hz, 1H), 0.68 (ddd, J=4.0, 7.6, 10.0 Hz, 1H).

(+)-hydroxyureamethylacylfulvene. (5) Hydroxyurea (7.5 mg, 0.098 mmol) was added to a solution of (+)-Irofulven (4) (12 mg, 0.049 mmol) in a mixture of acetone (1 mL) and 2M (aq) H$_2$SO$_4$ (1 mL) and the mixture was stirred for 24 h at room temperature before diluting with H$_2$O (15 mL) and EtOAc (15 mL), organics were separated and aqueous layer was extracted with EtOAc (2×10 mL). The combined organic extracts were washed with NaHCO$_3$ (aq) (10 mL) the brine (10 mL). The organic extracts were then dried over Na$_2$SO$_4$, concentrated to an oil and purified via silica gel column chromatography (column: 12 g silicycle; Eluent: gradient EtOAc 10-95% in hexane) to recover 6.6 mg (44%) of (+)-LP-184 (5) as a yellow solid and 3.0 mg (25%) of recovered (+)-Irofulven (4). ¹H-NMR (400 MHz) δ 7.03 (s, 1H), 6.86 (s, 1H), 5.37 (bs, 2H), 4.80 (d, J=14.8 Hz, 1H), 4.52 (d, J=14.5 Hz, 1H), 3.84 (bs, 1H), 2.17 (s, 3H), 2.08 (s, 3H), 1.47 (ddd, J=4.0, 6.4, 10.0 Hz, 1H), 1.35 (ddd, J=5.2, 6.4, 9.6 Hz, 1H), 1.35 (s, 3H), 1.34 (ddd, J=5.2, 7.6, 9.6 Hz, 1H), 0.68 (ddd, J=4.0, 7.6, 10.0 Hz, 1H).

Figure 5:
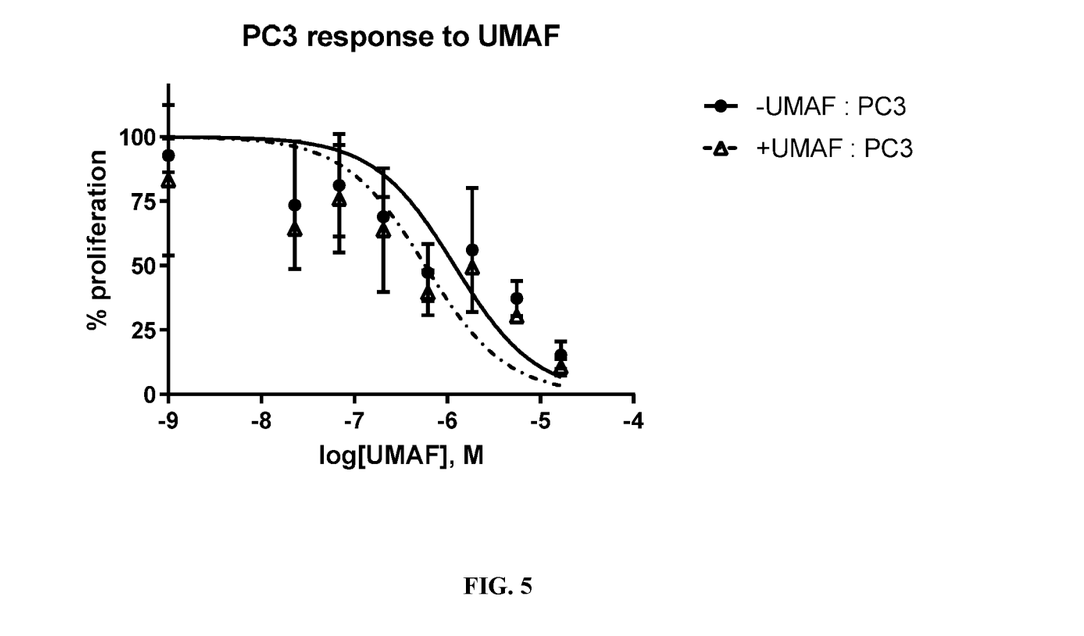
FIG. 5 show that the PC3 cell line has similarly sensitive to both enantiomeric forms of hydroxyureamethylacylfulvene, FIG. 6 show that the (+) enantiomer is more toxic to the OVCAR3 cell line, FIG. 7 show that the (+) enantiomer is more toxic to the SK-OV3 cell line.
Figure 6:
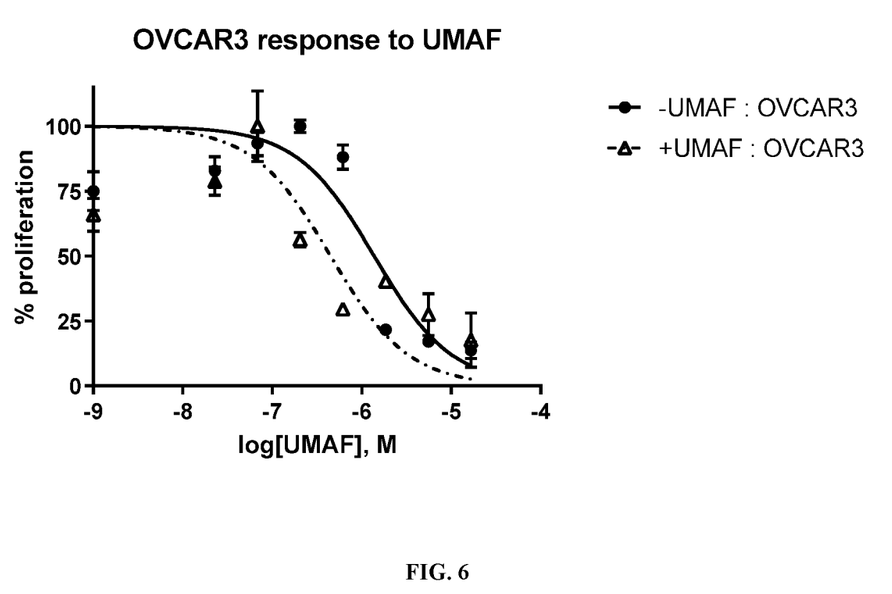
Figure 7:
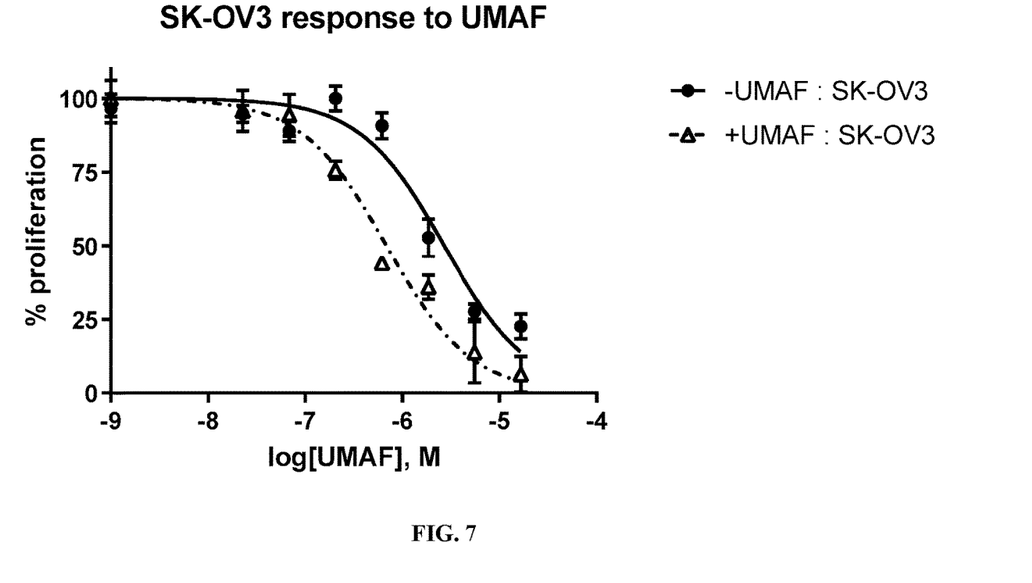
Figure 8:
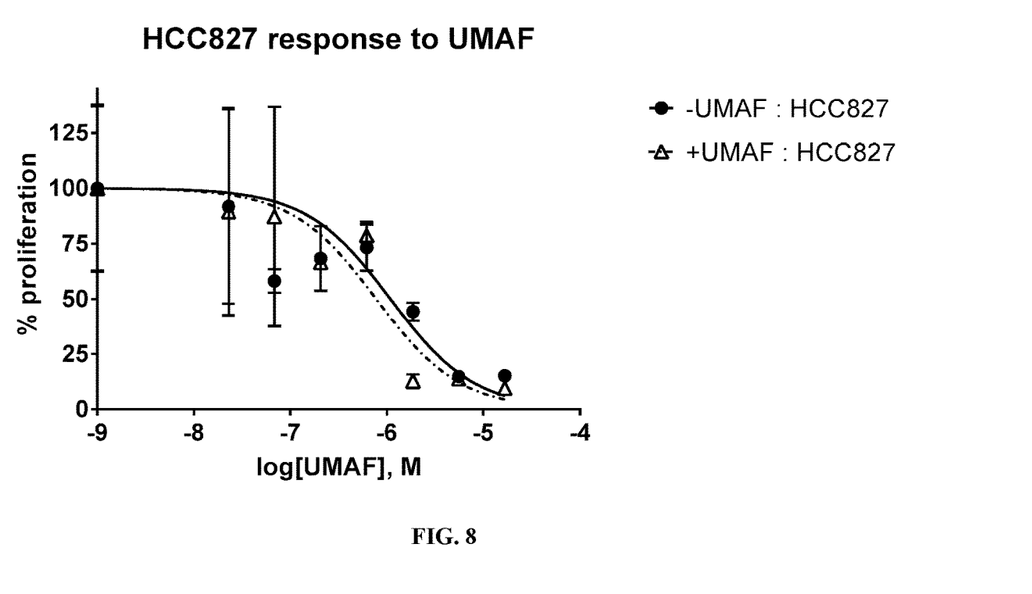
FIG. 8 show that the HCC827 cell line has similarly sensitive to both enantiomeric forms of hydroxyureamethylacylfulvene, and FIG. 9 show that the (+) enantiomer is more toxic to the H1975 cell line.
Figure 9:
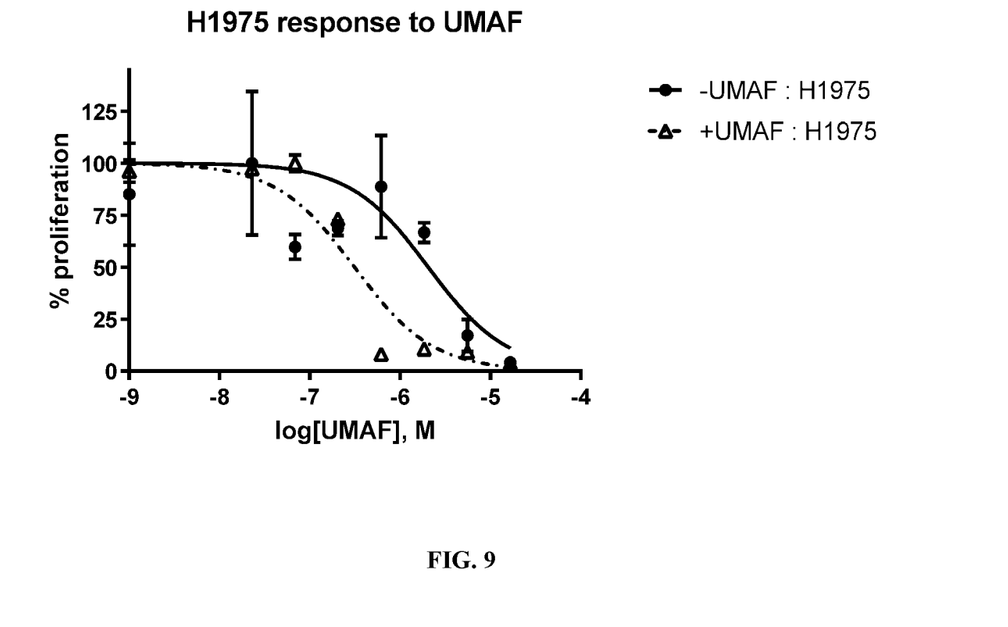

Cytotoxicity. The growth-inhibition activities of both purified UMAF (also referred to as UMAF in this example) optical enantiomers were studied in a standard 96-well cell-based assay using representative cell lines from prostate, ovarian, and lung cancers. The concentrations that cause a 50% inhibition of cell growth (GI$_{50}$) were determined using a luminescent vital assay reagent (CellTiter-Glo®, Promega Corporation). The growth inhibition curves as a function of UMAF concentration are shown from a representative assay. FIGS. 4, 6, 7, and 9 show that the (+) enantiomer is more toxic to DU145, OVCAR3, SK-OV3, and H1975 cell lines, respectively. FIGS. 5 and 8 show that the PC3 and HCC827 cell lines are similarly sensitive to both enantiomeric forms of the compound. The GI$_{50}$ concentrations of the two forms for the six cell lines are shown below.

| Activity of UMAF on cancer cell lines* | | | | | |
|---|---|---|---|---|---|
| Prostate | | Ovarian | | Lung | |
| DU145 | PC3 | OVCAR-3 | SK-OV3 | HCC827 | H1975 |
| (+)-UMAF 34.8 | 1,120 | 254 | 554 | 897 | 287 |
| (−)-UMAF 506 | 824 | 1,820 | 2,400 | 1,640 | 6,320 |

*Nanomolar concentrations of UMAF that inhibits 50% cell growth in a 3-day assay

The invention claimed is:

1. A compound having a positive optical rotation angle and having the following formula II:

2. A pharmaceutical composition comprising a compound according to claim 1 together with a pharmaceutically acceptable carrier.

3. A pharmaceutical composition comprising a compound of the following formula II having a positive optical rotation angle:

II or a pharmaceutically acceptable salt thereof.

4. The composition of claim 2, wherein the composition is free of other isomers of the compound.

5. The composition of claim 3, wherein the composition is free of other isomers of the compound.

* * * * *